United States Patent
Sluyterman van Langeweyde et al.

(10) Patent No.: US 10,271,990 B2
(45) Date of Patent: Apr. 30, 2019

(54) TREATMENT DEVICE FOR THE SURGICAL CORRECTION OF DEFECTIVE VISION OF AN EYE, METHOD FOR PRODUCING CONTROL DATA THEREFOR, AND METHOD FOR THE SURGICAL CORRECTION OF DEFECTIVE VISION OF AN EYE

(71) Applicant: Carl Zeiss Meditec AG, Jena (DE)

(72) Inventors: Georg Sluyterman van Langeweyde, Jena (DE); Gregor Stobrawa, Jena (DE); Christoph Russmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1330 days.

(21) Appl. No.: 14/351,854

(22) PCT Filed: Sep. 27, 2012

(86) PCT No.: PCT/EP2012/069108
§ 371 (c)(1),
(2) Date: Apr. 14, 2014

(87) PCT Pub. No.: WO2013/045564
PCT Pub. Date: Apr. 4, 2013

(65) Prior Publication Data
US 2014/0288538 A1    Sep. 25, 2014

(30) Foreign Application Priority Data
Sep. 30, 2011  (DE) .................. 10 2011 083 928

(51) Int. Cl.
*A61F 9/008*    (2006.01)

(52) U.S. Cl.
CPC ...... *A61F 9/00825* (2013.01); *A61F 9/00827* (2013.01); *A61F 9/00829* (2013.01);
(Continued)

(58) Field of Classification Search
CPC ....................................................... A61F 9/008
See application file for complete search history.

(56) References Cited

U.S. PATENT DOCUMENTS

| | | |
|---|---|---|
| 5,549,632 A | 8/1996 | Lai |
| 5,656,186 A | 8/1997 | Mourou et al. |

(Continued)

FOREIGN PATENT DOCUMENTS

| | | |
|---|---|---|
| DE | 695 00 997 T2 | 4/1998 |
| DE | 10 2006 053 120 A1 | 5/2008 |

(Continued)

*Primary Examiner* — Lynsey C Eiseman
(74) *Attorney, Agent, or Firm* — Christensen, Fonder, Dardi & Herbert PLLC (57) ABSTRACT

A treatment device for the surgical correction of defective vision in an eye. The device includes a laser apparatus controlled by a controller. The controller determines a desired correction of defective vision from measurement data of the eye to produce control data for the laser, and to control the laser to emit radiation according to the control data, such that a lenticule-shaped volume is isolated in the cornea. The controller computes a lenticule-shaped intended volume, the removal of which from the cornea leads to an actual correction of defective vision in an optical zone in the eye which differs from the desired correction more at the edge of the optical zone than at the center of the optical zone. The thickness of the lenticule-shaped intended volume is less than the thickness of a lenticule-shaped comparison volume, the removal of which would bring about the desired correction of defective vision.

7 Claims, 8 Drawing Sheets

(52) U.S. Cl.
CPC . *A61F 9/00838* (2013.01); *A61F 2009/00872* (2013.01); *A61F 2009/00878* (2013.01); *A61F 2009/00895* (2013.01)

(56) References Cited

U.S. PATENT DOCUMENTS

| | | |
|---|---|---|
| 5,683,379 A | 11/1997 | Hohla |
| 6,299,309 B1 | 10/2001 | Ruiz |
| 6,325,792 B1 | 12/2001 | Swinger et al. |
| 6,992,765 B2 | 1/2006 | Horvath et al. |
| 7,387,387 B2 | 6/2008 | Dai |
| 7,887,531 B2 | 2/2011 | Bartoli |
| 8,216,213 B2 | 7/2012 | Gross et al. |
| 2008/0319428 A1 | 12/2008 | Weichmann et al. |
| 2010/0331830 A1 | 12/2010 | Bischoff et al. |
| 2010/0331831 A1 | 12/2010 | Bischoff et al. |
| 2012/0016351 A1 | 1/2012 | Stobrawa et al. |
| 2013/0072916 A1 | 3/2013 | Bischoff et al. |

FOREIGN PATENT DOCUMENTS

| | | |
|---|---|---|
| DE | 10 2007 053 281 A1 | 5/2009 |
| DE | 10 2007 053 283 A1 | 5/2009 |
| DE | 10 2010 012 616 A1 | 9/2011 |
| EP | 1 034 756 A2 | 9/2000 |
| EP | 1 159 986 A2 | 12/2001 |
| EP | 0 785 761 B1 | 6/2002 |
| WO | WO 03/077795 A2 | 9/2003 |
| WO | WO 2004/032810 A2 | 4/2004 |
| WO | WO 2004/052253 A1 | 6/2004 |
| WO | WO 2006/009909 A1 | 1/2006 |
| WO | WO 2010/084162 A2 | 7/2010 |
| WO | WO 2010/084163 A1 | 7/2010 |

TREATMENT DEVICE FOR THE SURGICAL CORRECTION OF DEFECTIVE VISION OF AN EYE, METHOD FOR PRODUCING CONTROL DATA THEREFOR, AND METHOD FOR THE SURGICAL CORRECTION OF DEFECTIVE VISION OF AN EYE

PRIORITY CLAIM

The present application is a National Phase entry of PCT Application No. PCT/EP2012/069108, filed Sep. 27, 2012, which claims priority from German Application Number 102011083928.3, filed Sep. 30, 2011, the disclosures of which are hereby incorporated by reference herein in their entirety.

FIELD OF THE INVENTION

The invention relates to a treatment device for the surgical correction of defective vision in the eye wherein the treatment device has a laser apparatus controlled by a controller, which laser apparatus cuts corneal tissue by irradiation with laser radiation, wherein the controller is designed to determine a desired correction of defective vision from measurement data of the eye, to produce control data for the laser apparatus on the basis of the desired correction of defective vision, and to control the laser apparatus to emit the laser radiation into the cornea according to the control data such that a lenticule-shaped volume is thereby isolated in the cornea. The invention further relates to a method for producing control data for a laser apparatus of a treatment device for the surgical correction of defective vision in the eye which laser apparatus cuts corneal tissue by irradiation with laser radiation, wherein a desired correction of defective vision is determined from measurement data of the eye, control data for the laser apparatus are produced on the basis of the desired correction of defective vision and wherein the control data control the laser apparatus in operation to emit the laser radiation into the cornea such that a lenticule-shaped volume is thereby isolated in the cornea. Finally, the invention relates to a method for the surgical correction of defective vision in the eye in which a desired correction of defective vision is determined from measurement data of the eye, control data for a laser apparatus are produced on the basis of the desired correction of defective vision, corneal tissue is cut by irradiation with laser radiation from the laser apparatus according to the control data and a lenticule-shaped volume is thereby isolated in the cornea, and the lenticule-shaped volume is removed.

BACKGROUND OF THE INVENTION

Certain treatment devices and methods for surgical correction of defective vision of an eye are known, e.g., from WO 2010/084163 A1, as well as WO 2010/084162 A2.

If a hyperopia correction is desired, a regression due to post-operative epithelialization often occurs at the edge of the optical zone owing to the large channel depth and steep gradients after the lenticule-shaped volume has been removed from the cornea.

Only with very large optical zones does regression not occur. However, this disadvantageously leads to large cutting depths. However, owing to the required residual stromal thickness of e.g. at least 250 µm, these are limited, with the result that the possible uses thereof in the correction of hyperopia are restricted. Should, where appropriate, further corrections be required later, the residual stromal thickness must be correspondingly larger. Similar difficulties with regard to regression and/or residual thickness also arise in other vision defects to be corrected (such as, e.g., myopia).

SUMMARY OF THE INVENTION

Starting from here, an object of the invention is to develop a treatment device of the type named at the outset such that the described disadvantages can be overcome as far as possible. The same applies to a method for producing control data of the type named at the outset and a method for the surgical correction of defective vision in the eye of the type named at the outset.

According to the invention, the object is achieved by a treatment device for the surgical correction of defective vision in the eye, wherein the treatment device has a laser apparatus controlled by a controller, which laser apparatus cuts corneal tissue by irradiation with laser radiation, wherein the controller is designed to determine a desired correction of defective vision from measurement data of the eye, to produce control data for the laser apparatus on the basis of the desired correction of defective vision, and to control the laser apparatus to emit the laser radiation into the cornea according to the control data such that a lenticule-shaped volume is thereby isolated in the cornea, and wherein the controller computationally determines a lenticule-shaped intended volume, the removal of which from the cornea leads to an actual correction of defective vision in an optical zone in the eye which differs from the desired correction of defective vision more at the edge of the optical zone than in the center of the optical zone, and produces the control data such that they describe the lenticule-shaped intended volume, wherein the thickness of the lenticule-shaped intended volume is smaller than the thickness of a lenticule-shaped comparison volume, the removal of which from the cornea would bring about the desired correction of defective vision.

The treatment device according to the invention makes it possible to carry out a better correction of defective vision in the center of the optical zone than at the edge, which does lead to undercorrection at the edge of the optical zone, but this is only a slight disadvantage for the patient treated, as the effect of this undercorrection is not substantial for him. Advantageously, however, the maximum cutting depth can thereby be reduced, which can reduce a possible regression due to post-operative epithelialization.

The controller of the treatment device according to the invention can first computationally determine the lenticule-shaped comparison volume and then computationally reduce the thickness of the lenticule-shaped comparison volume in order to thus computationally determine the lenticule-shaped intended volume.

In the treatment device according to an embodiment of the invention, the controller can determine the lenticule-shaped intended volume, which is also called second lenticule-shaped intended volume in the following, such that the actual correction of defective vision brought about by the removal of the second lenticule-shaped intended volume corresponds, in the center of the optical zone, to the desired correction of defective vision. The area of undercorrection is thus moved (outwards) into an area which is essentially only used in a dark-adapted eye.

Furthermore, in the treatment device according to the invention, the controller can determine the second lenticule-shaped intended volume such that the actual correction of defective vision brought about by the removal of the second lenticule-shaped intended volume differs from the desired correction of defective vision such that the difference increases steadily in a radial direction from the center towards the edge of the optical zone. This can be implemented particularly well and shows good results and tolerances in the patients.

In order to determine the second lenticule-shaped intended volume, the controller can subtract a spherical aberration from the lenticule-shaped comparison volume, which is also called first lenticule-shaped intended volume in the following. In particular, combinations of spherical aberrations with higher-order aberrations (e.g., astigmatism) can also be subtracted from the first lenticule-shaped intended volume. A progression of curvature correction that is continuous over the radius can thus be achieved.

The controller can determine the second lenticule-shaped intended volume such that, after it is removed, the front of the cornea is prolate if the desired correction of defective vision is a hyperopia correction. If the desired correction of defective vision is a myopia correction, the controller can determine the second lenticule-shaped intended volume such that, after it is removed, the front of the cornea is oblate.

The treatment device according to the invention advantageously achieves the result that the correction of defective vision is greater in the center of the optical zone than at the edge of the optical zone.

Furthermore, an embodiment of the invention includes a method for producing control data for a laser apparatus of a treatment device for the surgical correction of defective vision in the eye, which laser apparatus cuts corneal tissue by irradiation with laser radiation, wherein a desired correction of defective vision is determined from measurement data of the eye, control data for the laser apparatus are produced on the basis of the desired correction of defective vision and wherein the control data control the laser apparatus in operation to emit the laser radiation into the cornea such that a lenticule-shaped volume is thereby isolated in the cornea, and wherein a lenticule-shaped intended volume is computationally determined, the removal of which from the cornea leads to an actual correction of defective vision in an optical zone in the eye which differs from the desired correction of defective vision more at the edge of the optical zone than in the center of the optical zone, and the control data are produced such that they describe the lenticule-shaped intended volume, wherein the thickness of the lenticule-shaped intended volume is smaller than the thickness of a lenticule-shaped comparison volume, the removal of which from the cornea would bring about the desired correction of defective vision.

An embodiment of the invention includes a method for the surgical correction of defective vision in the eye, in which a desired correction of defective vision is determined from measurement data of the eye, control data for a laser apparatus are produced on the basis of the desired correction of defective vision, corneal tissue is cut by irradiation with laser radiation from the laser apparatus according to the control data and a lenticule-shaped volume is thereby isolated in the cornea, and the lenticule-shaped volume is removed, and wherein a lenticule-shaped intended volume is computationally determined, the removal of which from the cornea leads to an actual correction of defective vision of an optical zone in the eye which differs from the desired correction of defective vision more at the edge of the optical zone than in the center of the optical zone, and the control data are produced such that they describe the lenticule-shaped intended volume, wherein the thickness of the lenticule-shaped intended volume is smaller than the thickness of a lenticule-shaped comparison volume, the removal of which from the cornea would bring about the desired correction of defective vision.

"Lenticule-shaped intended volume" may include a part of the cornea the removal of which brings about a change in the curvature of the cornea front surface and thus a correction of defective vision. "Lenticule-shaped comparison volume" may include a part of the cornea which, if it were actually to be removed, would bring about a change in the curvature of the cornea front surface and thus a correction of defective vision.

"Thickness" of the lenticule-shaped intended volume includes a locally varying thickness. The same applies to the thickness of the lenticule-shaped comparison volume. A smaller thickness of the lenticule-shaped intended volume thus also comprises in particular the case that the small thickness is only present in certain areas. The thickness of the lenticule-shaped intended volume taken as a whole can also be smaller than the thickness of the lenticule-shaped comparison volume.

Advantageous developments of a method according to the invention for producing control data as well as the method according to the invention for the surgical correction of defective vision in the eye are given in the dependent method claims.

In particular, a method according to an embodiment of the invention for the surgical correction of defective vision in the eye can also include the step of removing the isolated lenticule-shaped volume.

By the optical zone is meant here e.g. the area of the cornea in which the correction is to be carried out. In particular, the optical zone can be the projection of the dilated pupil and thus in the case of a dark-adapted eye onto the cornea.

Furthermore, an embodiment of the invention includes a treatment device for the surgical correction of defective vision in the eye, wherein the treatment device has a laser apparatus controlled by a controller, which laser apparatus cuts corneal tissue by irradiation with laser radiation, wherein the controller is designed to determine a desired correction of defective vision from measurement data of the eye, to produce control data for the laser apparatus on the basis of the desired correction of defective vision, and to control the laser apparatus to emit the laser radiation into the cornea according to the control data such that a lenticule-shaped volume is thereby isolated in the cornea. The controller computationally determines a first lenticule-shaped intended volume, the removal of which from the cornea would bring about the desired correction of defective vision in an optical zone in the eye, computationally reduces the thickness of the first lenticule-shaped intended volume, and thus determines a second lenticule-shaped intended volume, the removal of which from the cornea leads to an actual correction of defective vision which differs from the desired correction of defective vision more at the edge of the optical zone than in the center of the optical zone, and produces the control data such that they describe the second lenticule-shaped intended volume.

Furthermore, an embodiment of the invention includes a method for producing control data for a laser treatment device for the surgical correction of defective vision in the eye, which laser apparatus cuts corneal tissue by irradiation with laser radiation, wherein a desired correction of defective vision is determined from measurement data of the eye, control data for the laser apparatus are produced on the basis of the desired correction of defective vision and wherein the control data control the laser apparatus in operation to emit the laser radiation into the cornea such that a lenticule-shaped volume is thereby isolated in the cornea, and wherein a first lenticule-shaped intended volume is computationally determined, the removal of which from the cornea would bring about the desired correction of defective vision in a zone in the eye, the thickness of the first lenticule-shaped intended volume is computationally reduced, and thus a second lenticule-shaped intended volume is determined, the removal of which from the cornea leads to an actual correction of defective vision which differs from the desired correction of defective vision more at the edge of the optical zone than in the center of the optical zone, and the control data are produced such that they describe the second lenticule-shaped intended volume.

An embodiment of the invention includes a method for the surgical correction of defective vision in the eye, in which a desired correction of defective vision is determined from measurement data of the eye, control data for a laser apparatus are produced on the basis of the desired correction of defective vision, corneal tissue is cut by irradiation with laser radiation from the laser apparatus according to the control data and a lenticule-shaped volume is thereby isolated in the cornea, and the lenticule-shaped volume is removed, and wherein a first lenticule-shaped intended volume is computationally determined, the removal of which from the cornea would bring about the desired correction of defective vision of an optical zone in the eye, the thickness of the first lenticule-shaped intended volume is computationally reduced, and thus a second lenticule-shaped intended volume is determined, the removal of which from the cornea leads to an actual correction of defective vision which differs from the desired correction of defective vision more at the edge of the optical zone than in the center of the optical zone, and the control data are produced such that they describe the second lenticule-shaped intended volume.

The features described here can be combined as desired with one another, providing they do not contradict each other technically.

Methods according to the invention for producing the control data can be carried out without recourse to human involvement. In particular they can be carried out by a computer which carries out methods according to embodiments of the invention under the control of a program for the invention and determines control data for the laser apparatus from corresponding presets. In particular when determining control data there may be no need for the participation of a doctor as there may be no therapeutic procedure involved in determining the control data. This takes place only when the previously determined control data are used.

Where a method or individual steps of a method for determining control data for the surgical correction of defective vision are described in this description, the method or individual steps of the method can be carried out using a correspondingly designed device. This applies analogously to the explanation of the mode of operation of a device which carries out the method steps. To this extent, device and method features of this description are equivalent. In particular it is possible to realize the method with a computer on which a corresponding program according to the invention is executed.

BRIEF DESCRIPTION OF THE DRAWINGS

The invention is explained in even more detail below, by way of example, with reference to the drawings in which.

DETAILED DESCRIPTION

Figure 1:
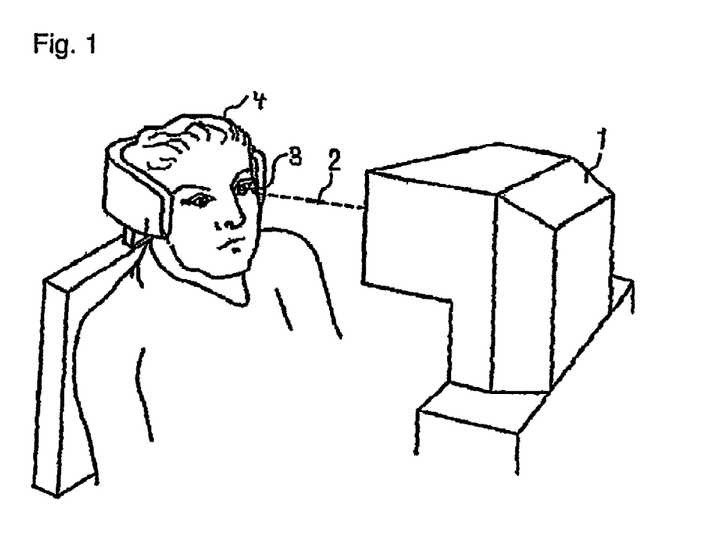
FIG. 1 is a schematic representation of a treatment device or of a treatment apparatus for the correction of defective vision.

FIG. 1 shows a treatment apparatus 1 for an eye-surgery method which is similar to that described in EP 1 159 986 A2 and in U.S. Pat. No. 5,549,632. By means of a treatment laser radiation 2 the treatment apparatus 1 brings about a correction of defective vision in an eye 3 of a patient 4. Defective vision can include hyperopia, myopia, presbyopia, astigmatism, mixed astigmatism (astigmatism in which there is hyperopia in one direction and myopia in a direction lying at right angles thereto), aspherical errors and higher-order aberrations. In the embodiment described, the treatment laser radiation 2 is conveyed as a pulsed laser beam focussed into the eye 3. The pulse duration in this case is, e.g., in the femtosecond range, and the laser radiation 2 acts by means of non-linear optical effects in the cornea. The laser beam has e.g. 50 to 800 fs short laser pulses (preferably 100-400 fs) with a pulse repetition frequency of between 10 and 500 kHz. In the embodiment example described, the components of the apparatus 1 are controlled by an integrated control unit, which, however, can of course also be formed as a stand-alone unit.

Before the treatment apparatus is used, the defective vision of the eye 3 is measured with one or more measuring devices.

Figure 2:
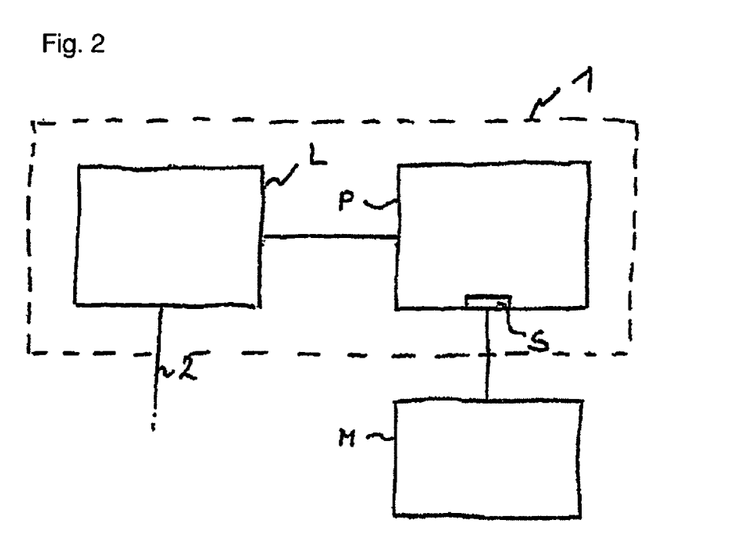
FIG. 2 is a schematic representation with regard to the structure of the treatment apparatus of FIG. 1.

FIG. 2 shows the treatment apparatus 1 schematically. In this variant it has at least two devices or modules. A laser apparatus L emits the laser beam 2 onto the eye 3. The operation of the laser apparatus L in this case is fully automatic, i.e., in response to a corresponding start signal the laser apparatus L starts to deflect the laser beam 2 and produces cutting surfaces which are constructed in a manner to be described below and isolate a volume in the cornea. The laser apparatus L receives the control data necessary for operation beforehand from a planning device P as a control data set, via control lines that are not described in more detail. Transmission takes place prior to operation of the laser apparatus L. Naturally, communication can also be wireless. As an alternative to direct communication, it is also possible to arrange the planning unit P physically separated from the laser unit L, and to provide a corresponding data transmission channel.

The control data set may be transmitted to the treatment apparatus 1 and operation of the laser apparatus L may be blocked until there is a valid control data set at the laser apparatus L. A valid control data set can be a control data set which in principle is suitable for use with the laser apparatus L of the treatment device 1. Additionally, however, the validity can also be linked to further tests being passed, for example, whether details additionally stored in the control data set concerning the treatment apparatus 1, e.g., an appliance serial number, or concerning the patient, e.g., a patient identification number, correspond to other details that, for example, have been read out or input separately at the treatment device as soon as the patient is in the correct position for the operation of the laser apparatus L.

The planning unit P produces the control data set that is made available to the laser unit L for carrying out the operation, from measurement data which have been determined for the eye to be treated. They are supplied to the planning unit P via an interface S and, in the embodiment example represented, come from a measuring device M which has previously taken measurements of the eye of the patient 4. Naturally, the measuring device M can transfer the corresponding measurement data to the planning device P in any desired manner.

Transmission can be by means of memory chips (e.g. by USB or memory stick), magnetic storage (e.g., disks), or other data storage devices, by radio (e.g., WLAN, UMTS, Bluetooth) or wired connection (e.g., USB, Firewire, RS232, CAN-Bus, Ethernet etc.). The same naturally, applies with regard to the data transmission between planning device P and laser apparatus L.

A direct radio or wired connection of the measuring device M to the treatment device 1 with regard to the data transmission which can be used in a variant has the advantage that the use of incorrect measurement data is excluded with the greatest possible certainty. This applies in particular if the patient is transferred from the measuring device M or measuring devices to the laser apparatus L by means of a support device (not represented in the figure) which interacts with the measuring device M and the laser apparatus L such that the respective devices recognize whether the patient 4 is in the respective position for measurement or introduction of the laser radiation 2. By bringing the patient 4 from the measuring device M to the laser apparatus L the transmission of the measurement and defective-vision data to the treatment device 1 can also take place simultaneously.

In an embodiment, it is ensured by suitable means that the planning device P always produces the control data set belonging to the patient 4 and an erroneous use of an incorrect control data set for a patient 4 is as good as excluded.

Figure 3:
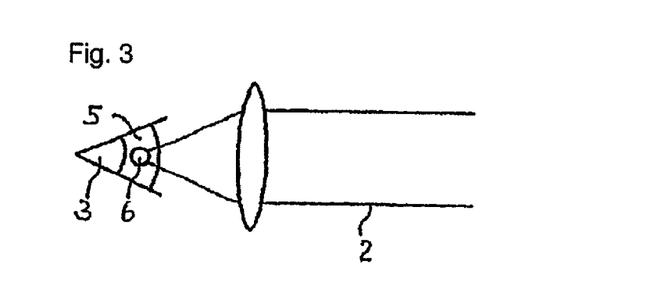
FIG. 3 is a presentation showing the principle of introducing pulsed laser radiation into the eye when correcting defective vision with the treatment apparatus of FIG. 1.

The mode of operation of the laser beam 2 is indicated schematically in FIG. 3. The treatment laser beam 2 is focussed into the cornea 5 of the eye 3 by means of a lens system that is not described in more detail. As a result there forms in the cornea 5 a focus that covers a spot 6 and in which the energy density of the laser radiation is so high that, in combination with the pulse length, a non-linear effect in the eye results. For example, each pulse of the pulsed laser radiation 2 can produce at the respective spot 6 an optical breakthrough in the cornea 5 which, in turn, initiates a plasma bubble, indicated schematically in FIG. 3. As a result, tissue in the cornea 5 is separated owing to this laser pulse. When a plasma bubble forms, the tissue layer separation covers a larger region than the spot 6 covered by the focus of the laser radiation 2, although the conditions for producing the breakthrough are achieved only in the focus. In order for an optical breakthrough to be produced by every laser pulse, the energy density, i.e., the fluence, of the laser radiation must be above a certain threshold value which is dependent on pulse length. This relationship is known to a person skilled in the art from, for example, DE 695 00 997 T2.

Alternatively, a tissue-separating effect can also be produced by the pulsed laser radiation by emitting several laser radiation pulses in a region, wherein the spots 6 overlap for several laser radiation pulses. Several laser radiation pulses then interact to achieve a tissue-separating effect.

The type of tissue separating which the treatment apparatus 1 uses is, however, not further relevant for the description below, although pulsed treatment laser radiation 2 is described in this description. For example a treatment apparatus 1 such as is described in WO 2004/032810 A2 can be used. A large number of laser-pulse foci form a cutting surface in the tissue, the shape of which depends on the pattern with which the laser-pulse foci are/become arranged in the tissue. The pattern predetermines target points for the focus position at which one or more laser pulse(s) is (are) emitted and defines the shape and position of the cutting surface.

In order to now carry out a correction of defective vision, material is removed from a region within the cornea 5 by means of the pulsed laser radiation by cutting tissue layers there which isolate the material and then make it possible for material to be removed. The removal of material brings about a change in the volume of the cornea, which results in a change in the optical imaging action of the cornea 5, which is calculated based on the previously determined desired correction of defective vision, as further described in detail below. To isolate the volume to be removed, the focus of the laser radiation 2 is directed onto target points in the cornea 5, generally in an area which is located beneath the epithelium and the Bowman's membrane and above the Descemet's membrane and the endothelium. For this purpose the treatment apparatus 1 has a mechanism for shifting the position of the focus of the laser radiation 2 in the cornea 5. This is shown schematically in FIG. 4.

Figure 4:
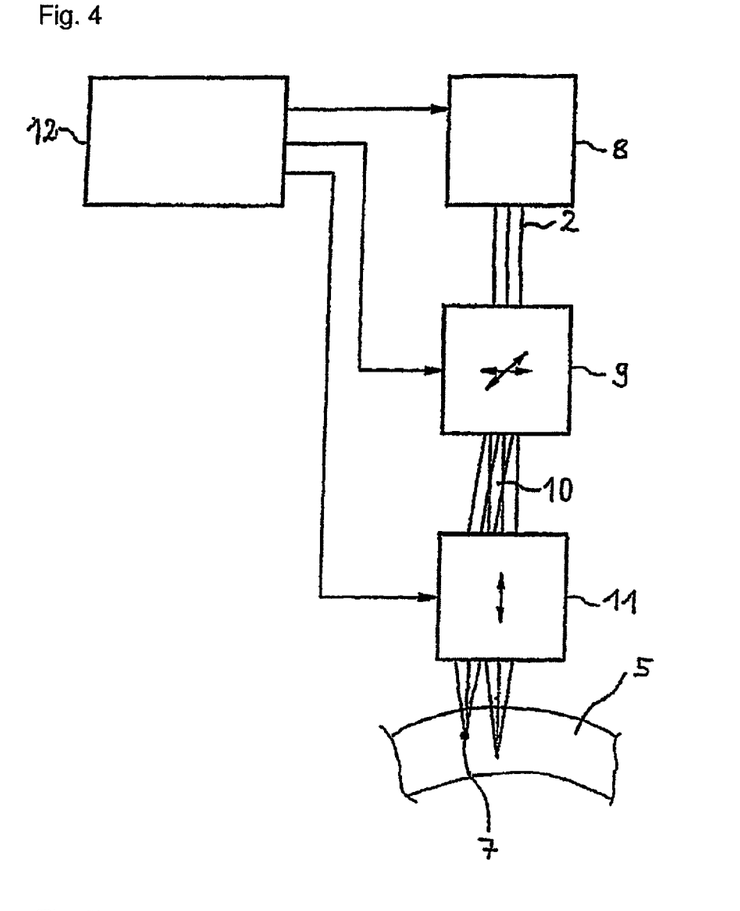
FIG. 4 is a further schematic representation of the treatment apparatus of FIG. 1.

In FIG. 4, elements of the treatment apparatus 1 are shown only if they are necessary to understand the shifting of the focus. As already mentioned, the laser radiation 2 is focussed to a focus 7 in the cornea 5 and the position of the focus 7 in the cornea 5 is moved, with the result that energy from laser radiation pulses will enter the tissue of the cornea 3 focussed at various points to produce cutting surfaces. The laser radiation 2 is provided by a laser 8 as pulsed radiation. An xy scanner 9, which, in a variant, is realized by two substantially orthogonally deflecting galvanometric mirrors, deflects the laser beam coming from the laser 8 in two dimensions, with the result that there is a deflected laser beam 10 after the xy scanner 9. The xy scanner 9 thus brings about a shifting of the focus 7 substantially perpendicular to the main direction of incidence of the laser radiation 2 into the cornea 5. To adjust the depth position a z scanner 11, which is formed, for example, as an adjustable telescope, is provided in addition to the xy scanner 9. The z scanner 11 ensures that the z position of the focus 7, i.e., its position on the optical axis of incidence, is changed. The z scanner 11 can be arranged before or after the xy scanner 9. However, it is possible to design the scanner such that it can set the position in all three directions (x-, y- and z-direction). The coordinates designated x, y, z in the following thus relate to the deflection of the position of the focus 7.

The allocation of the individual coordinates to the spatial directions is not essential for the operating principle of the treatment apparatus 1; however, to simplify the description, in the following the coordinate along the optical axis of incidence of the laser radiation 2 is always designated z, and x and y designate two coordinates orthogonal to one another in a plane perpendicular to the direction of incidence of the laser beam. It is naturally known to a person skilled in the art that the position of the focus 7 in the cornea 5 can also be described three-dimensionally by other coordinate systems, in particular the coordinate system need not be a rectangular coordinate system. Thus it is not essential for the xy scanner 9 to deflect axes that are at right angles to one another; rather, any scanner capable of shifting the focus 7 in a plane in which the axis of incidence of the optical radiation does not lie can be used. Oblique-angled coordinate systems are thus also possible.

Further, non-Cartesian coordinate systems can also be used to describe, or control, the position of the focus 7, as is also explained further below. Examples of such coordinate systems are ball coordinates (also called spherical coordinates) as well as cylindrical coordinates.

To control the position of the focus 7, the xy scanner 9, as well as the z scanner 11, which together realize a specific example of a three-dimensional focus-shifting device, are controlled by a control apparatus 12 via lines not described in more detail. The same applies to the laser 8. The control apparatus 3 ensures a suitably synchronous operation of the laser 8 as well as the three-dimensional focus-shifting device, realized by way of example by the xy scanner 9 and the z scanner 11, with the result that the position of the focus 7 is shifted in the cornea 5 such that, ultimately, a specific volume of material is isolated, wherein the subsequent volume removal brings about a correction of defective vision.

The control apparatus 12 operates according to predetermined control data which predetermine the target points for shifting the focus. The control data are generally combined in a control data set. In one embodiment, this predetermines the coordinates of the target points as a pattern, wherein the sequence of the target points in the control data set defines the serial arrangement of the focus positions alongside one another and thus, ultimately, a path curve (also referred to here for short as a path). In one embodiment, the control data set contains the target points as specific setting values for the focus-shifting mechanism, e.g., for the xy scanner 9 and the z scanner 11. To prepare the eye-surgery procedure, thus before the actual operation can be carried out, the target points and preferably also their sequence in the pattern are determined.

Firstly, the volume to be isolated in the cornea 5 and later removed must be defined. For this, as already described with reference to FIG. 2, it is necessary to ascertain the correction need.

Figure 5:
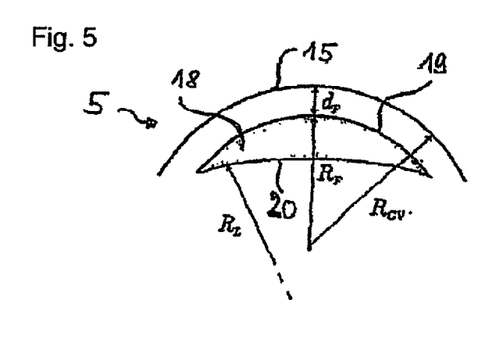
FIG. 5 is a schematic sectional representation through the cornea showing a volume to be removed for the correction of defective vision.
Figure 6:
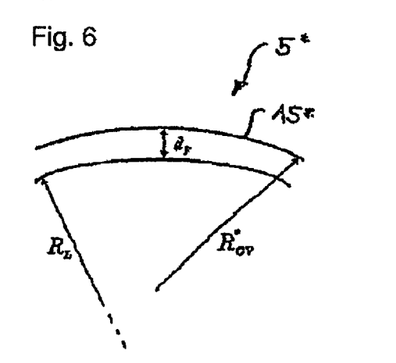
FIG. 6 is a section through the cornea after removal of the volume of FIG. 5.

With regard to the nomenclature used in this description it may be noted that the addition of an asterisk to values indicates that these are values which are obtained after a correction. On the justified assumption that a change in the thickness of the cornea 5 substantially modifies the radius of curvature of the front 15 of the cornea facing the air, but not the radius of curvature of the back 16 of the cornea adjacent to the inside of the eye, the radius of curvature $R_{CV}$ of the front 15 of the cornea is modified by the volume removal (FIGS. 5 and 6). Because of the modified curvature of the front, the cornea 5 reduced by the volume, with changed cornea surface 15*, has a correspondingly changed imaging action, with the result that there is now a corrected focus on the retina of the eye 3.

The boundary surface isolating the volume can be defined for the volume the removal of which brings about the desired change in curvature of the cornea front surface 15. What basic shape the volume is to have is to be taken into account.

In a first variant, a free surface is defined by numerical methods known to a person skilled in the art, which free surface circumscribes the volume the removal of which brings about the change in curvature. For this, the volume thickness required for the desired modification in curvature is determined along the z axis. The volume results from this as a function of the location (e.g., in cylinder coordinates), and its boundary surface from this in turn.

On the other hand, an analytical calculation is delivered by the following variant, already discussed in DE 10 2006 053 120 A1, in which the boundary surface of the volume is essentially built up from two part-surfaces: an anterior part-surface facing the cornea surface 15 and an opposite posterior part-surface. FIG. 5 shows the corresponding relationships. The volume 18 is limited towards the cornea front surface 15 by an anterior cutting surface 19, which is at a constant distance $d_F$ below the cornea front surface 15. This anterior cutting surface 19 is also called flap surface 19 by analogy with the laser keratomes as it serves there, in combination with an opening section towards the edge, to enable a flap-shaped lamella to be raised from the cornea 5 from the cornea 5 lying beneath it. This way of removing the previously isolated volume 18 is naturally also possible here.

The anterior cutting surface 19 is preferably spherical, as a radius of curvature which is smaller by the thickness of a lamella $d_F$ than the radius of curvature $R_{CV}$ can then be given for it.

To the rear, the volume 18 which is to be removed from the cornea 5 is limited by a posterior cutting surface 20 which already basically cannot be at a constant distance from the cornea front surface 15. The posterior cutting surface 20 will therefore be formed such that the volume 18 is present in the form of a lenticule, which is why the posterior cutting surface 20 is also called lenticule surface. It is drawn in FIG. 5 by way of example as a likewise spherical surface with a radius of curvature $R_L$, wherein naturally the center of this curvature does not coincide with the center of curvature of the likewise spherical cornea front surface 15 in FIG. 5. The two surfaces 19, 20 are preferably connected at the edge by a lenticule edge surface in order to completely bound the volume to be removed and simultaneously guarantee a minimum thickness at the edge.

Figure 7:
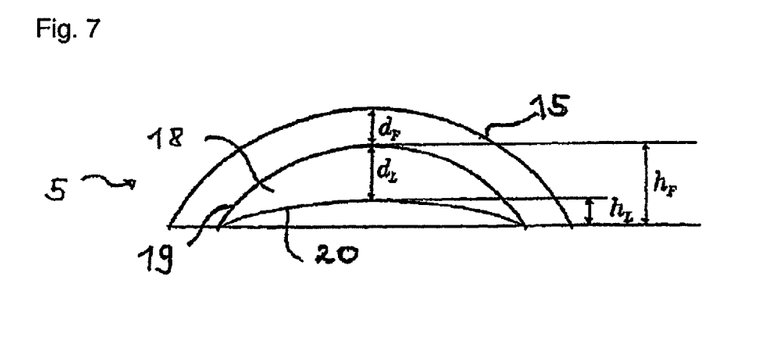
FIG. 7 is a sectional representation similar to that of FIG. 5.

FIG. 6 shows the situation after the volume 18 has been removed. The radius of the modified cornea front surface 15* is now $R_{CV}*$ and can, for example, be calculated according to the contents of DE 10 2006 053 120 A1, WO 2010/084162 A2 and WO 2010/084163 A1. The thickness $d_L=\Delta z(r=0,\varphi)$ of the removed volume 18 governs the change in radius, as illustrated by FIG. 7. The lenticule surface is simplified to be spherical in this figure. Consequently, the height $h_F$ of the spherical cap defined by the flap surface 19, the height $h_L$ of the spherical cap defined by the lenticule surface 20 and the thickness $d_L$ of the volume 18 to be removed are also drawn in as further values.

On the basis of the constant distance between cornea front surface 15 and flap surface 19, the lenticule surface 20 defines the curvature pattern of the cornea front surface 15* after the volume 18 has been removed.

The formation shown in the figures of the volume 18, as limited by a flap surface 19 at a constant distance from the cornea front surface 15 as well as by a lenticule surface 20, is only one variant for limiting the volume 18. However, it has the advantage that the optical correction is defined essentially by only one surface (the lenticule surface 20), with the result that the analytical description of the other part-surface of the boundary surface is simple.

Furthermore, safety margins with regard to the distance from the volume to the cornea front surface 15 and cornea back surface 16 are optimal. The residual thickness $d_F$ between flap surface 19 and cornea front surface 15 can be set constantly to a value of, for example, 50 to 200 µm. In particular it can be chosen such that the pain-sensitive epithelium remains in the lamella, which is formed by the flap surface 19 beneath the cornea front surface 15. The formation of the spherical flap surface 19 is also continuous with previous keratometer sections, which is advantageous in terms of acceptance of the method.

After the cutting surfaces 19 and 20 have been produced, the thus-isolated volume 18 is then removed from the cornea 5. This is represented schematically in FIG. 8, which also shows that the cutting surfaces 19 and 20 are produced by the action of the treatment laser beam incident in a cone of focus 21, for example, by the arrangement of plasma bubbles alongside one another, with the result that in a preferred embodiment the flap surface 19 and the lenticule surface 20 are produced by suitable three-dimensional shifting of the focus position of the pulsed laser radiation 2.

Figure 8:
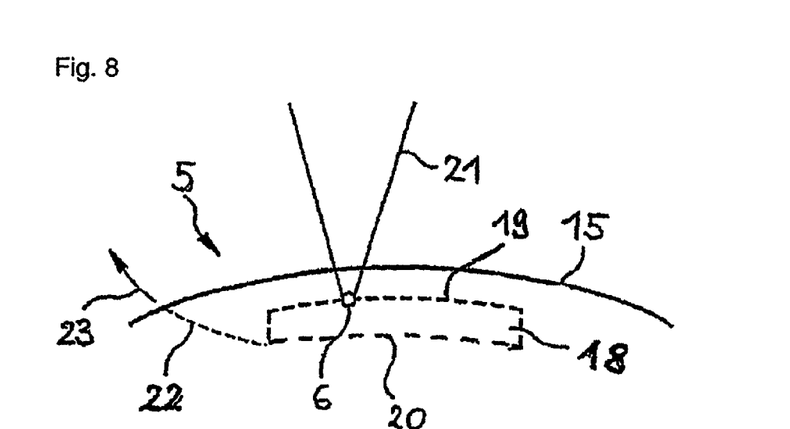
FIG. 8 is a schematic sectional representation through the cornea to illustrate the volume removal.

Alternatively in a simplified embodiment, however, merely the flap surface 19 can also be formed, by means of pulsed laser radiation, by target points which define the curved cutting surface 19 at a constant distance from the cornea front surface 15, and the lenticule-shaped volume 18 is removed by laser ablation, for example by using an excimer laser beam. For this, the lenticule surface 20 can be defined as boundary surface of the area removed, although this is not essential. The treatment apparatus 1 then operates like a known laser keratome, but the cutting surface 19 is produced using curved cornea. The previously or subsequently described features are also possible in such variants, in particular as regards the determination of the boundary surface, its geometric definition and the determination of control parameters.

If both the lenticule surface 20 and the flap surface 19 are produced by means of pulsed laser radiation, it is expedient to form the lenticule surface 20 before the flap surface 19, as the optical result in the lenticule surface 20 is better (or even achieved in the first place) if there has still been no change in the cornea 5 above the lenticule surface 20.

The precise shape of the lenticule 18 to be removed is determined according to the invention as follows.

In a first step S1 (FIG. 9), the control apparatus 12 (or the controller 12), which can contain the planning module P, determines the desired correction of defective vision on the basis of measurement data of the eye 3 to be corrected (the measurement data can originate from the measuring device M, as indicated by arrow P1). If, e.g., hyperopia is measured, the curvature $R^*_{CV}$ to be achieved of the then-modified cornea front surface 15* is determined in step S1 in order to correct the hyperopia measured.

Figure 9:
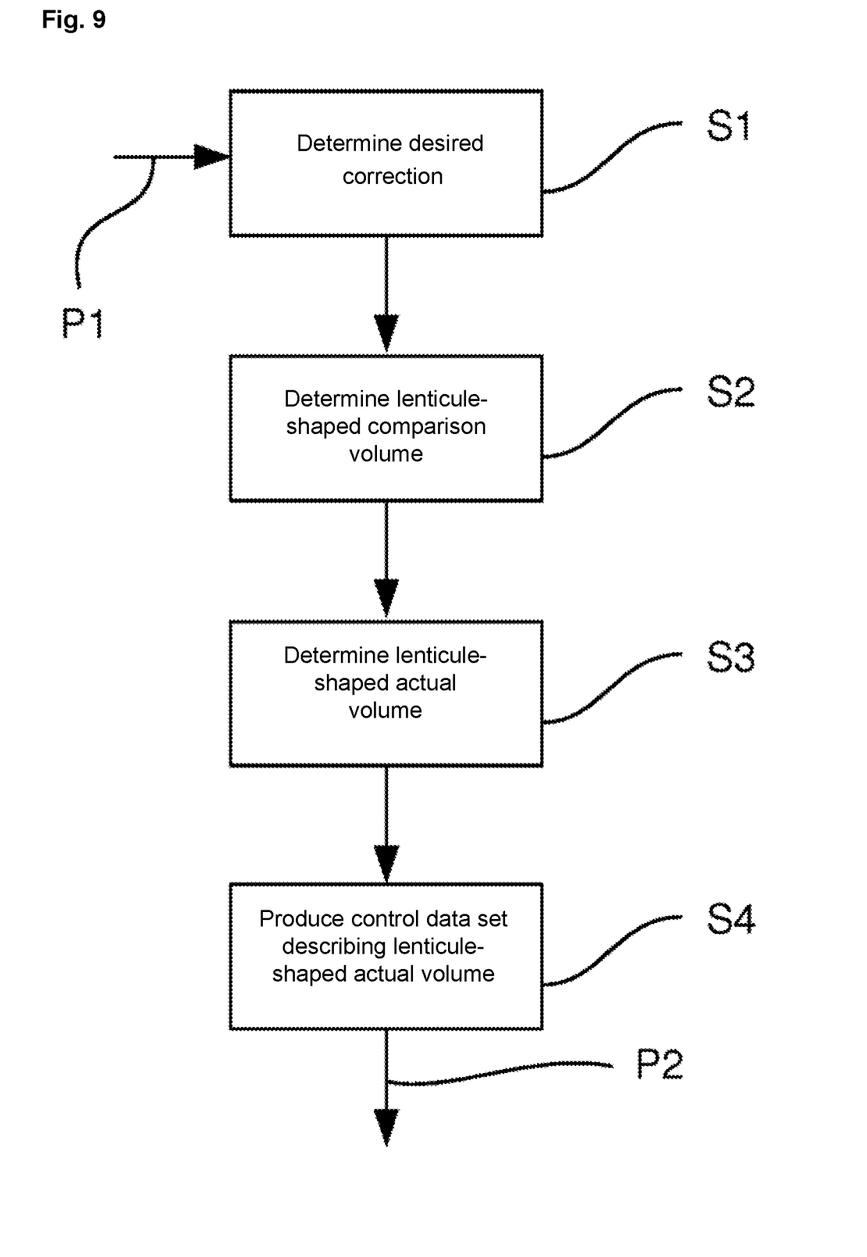
FIG. 9 is a flow diagram to explain a method according to the invention.

In step S2, a lenticule-shaped intended volume which should be removed from the cornea 18 in order to achieve the desired hyperopia correction is then determined.

In the subsequent step S3, the thickness of the first lenticule-shaped intended volume is computationally reduced and a second lenticule-shaped intended volume is thus determined. The second lenticule-shaped intended volume and thus the reduction in thickness is carried out such that it increases as the distance from the center of the optical zone increases.

Figure 10:
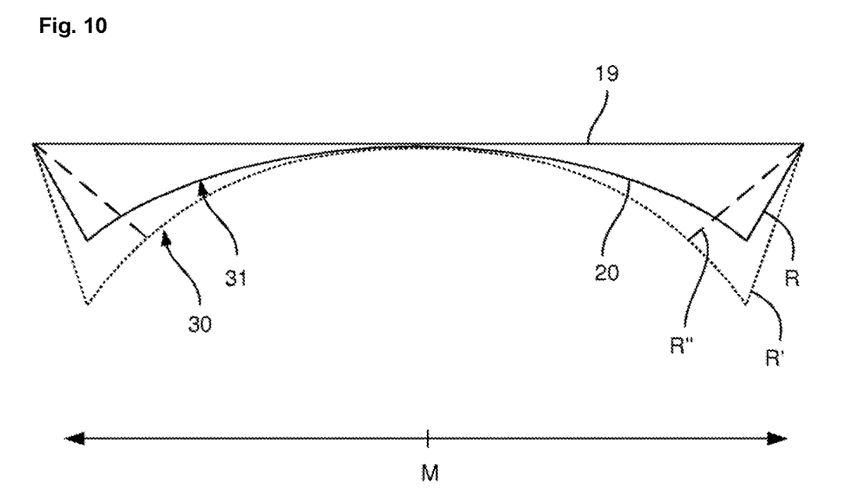
FIG. 10 is a diagram to explain the profile determined for the second lenticule-shaped intended volume.

This procedure is represented schematically in FIG. 10. The profile shape for the hyperopia correction according to step S2 is represented as dotted line 30, wherein the flap surface 19 is represented here as a flat surface for the sake of simplicity, as the correction essentially depends on the removed volume and thus on the thickness profile of the lenticule-shaped volume. The profile shape according to the second lenticule-shaped intended volume with reduced thickness is drawn in as solid line 31. As can be seen from the representation, the thickness of the second lenticule-shaped intended volume decreases radially from the center M towards the outside in comparison with the thickness of the first lenticule-shaped intended volume 30. This can be achieved, e.g., by adding to the profile of the first lenticule-shaped intended volume a spherical aberration, the sign of which is chosen such that a stronger hyperopia correction occurs in the center than at the edge of the optical zone.

As can further be seen from FIG. 10, the flap surface 19 and the lenticule surface 20 are connected at their edges via an annular lateral face R. This lateral face is often also called the transition zone. If this transition zone for the profile shape 30 is not formed as edge R', but as edge R", a maximum lenticule thickness is in fact also achieved which is comparable to the maximum lenticule thickness according to profile 31. However, in this case the diameter range, or the radial distance from the center M, is significantly smaller than in the case of the profile 31 according to the invention, which would be a disadvantage.

In step S4 (FIG. 9), the control data are then produced which describe the second lenticule-shaped intended volume and which are supplied to the laser apparatus L (as indicated by arrow P2) as a control data set. When the method according to the invention is carried out, the corresponding lenticule 18 is then removed from the cornea, with the result that a pre-operatively spherical cornea 5 is post-operatively prolate, i.e., post-operatively it is curved more in the center than at the edge of the optical zone.

This results in a lower maximum cutting depth achieved at the edge of the optical zone. This can be clearly seen in FIG. 10. Furthermore, the maximum gradients can also be reduced.

The embodiment shown in FIG. 10 is thus effectively an undercorrection if the pupil is dilated (scotopic) and a full correction when the pupil is small (photopic). Mesopically (at intermediate pupil size), the effect of the undercorrection is smaller. The patient can (if not yet presbyopic) easily compensate for this undercorrection by accommodation.

Figure 11:
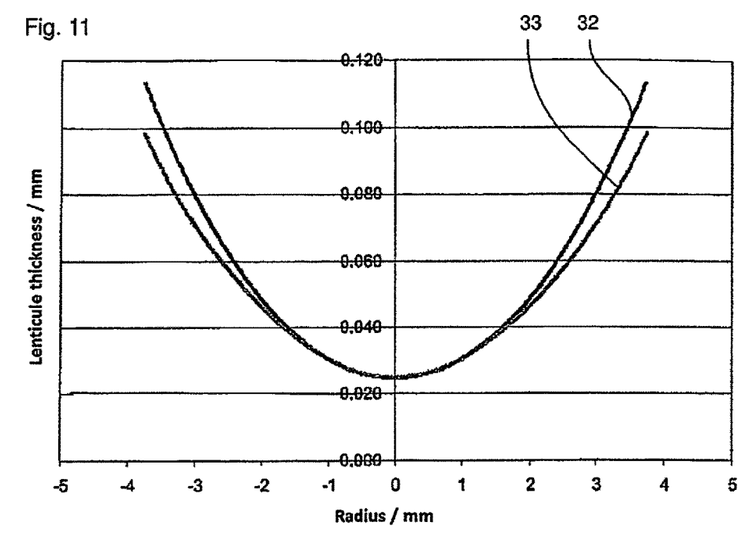
FIG. 11 is a representation to explain the determined lenticule thickness according to the invention.

In FIG. 11, the lenticule thickness in mm is plotted against the radius (i.e., the radial distance from the center M) in mm, wherein the curve 32 shows the lenticule thickness for the first lenticule-shaped intended volume and the curve 33 shows the lenticule thickness for the second lenticule-shaped intended volume. It can be seen from this that the maximum lenticule thickness in the second lenticule-shaped intended volume is 15 µm smaller than in the first lenticule-shaped intended volume. Eyes with a smaller cornea thickness can thus also be corrected with the method according to the invention.

Figure 12:
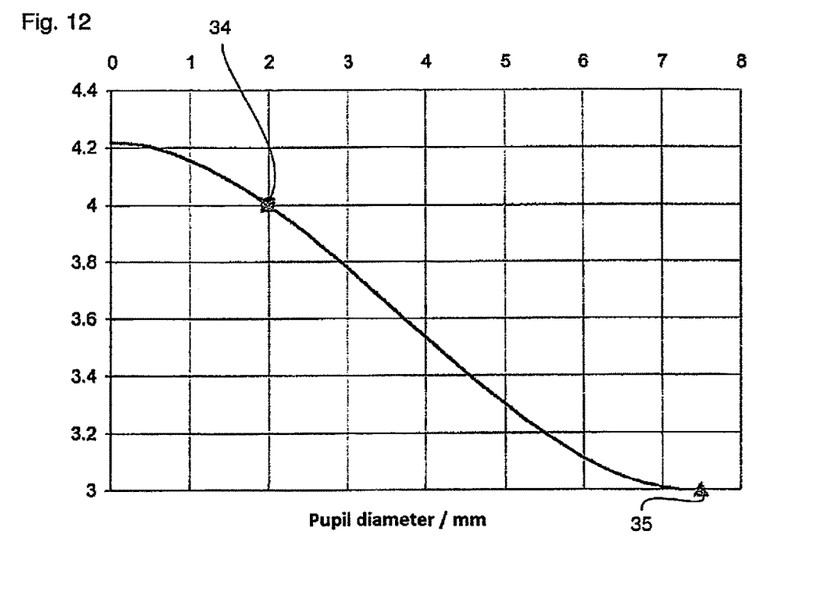
FIG. 12 is a representation to explain the correction of defective vision according to the invention in the case of a hyperopia correction.

In FIG. 12, the effective change in refractive power in diopters is plotted against the pupil diameter in mm, wherein the photopic pupil (2-mm pupil) is represented as point 34 and the scotopic pupil (7.5-mm pupil) is represented as point 35.

Figure 13:
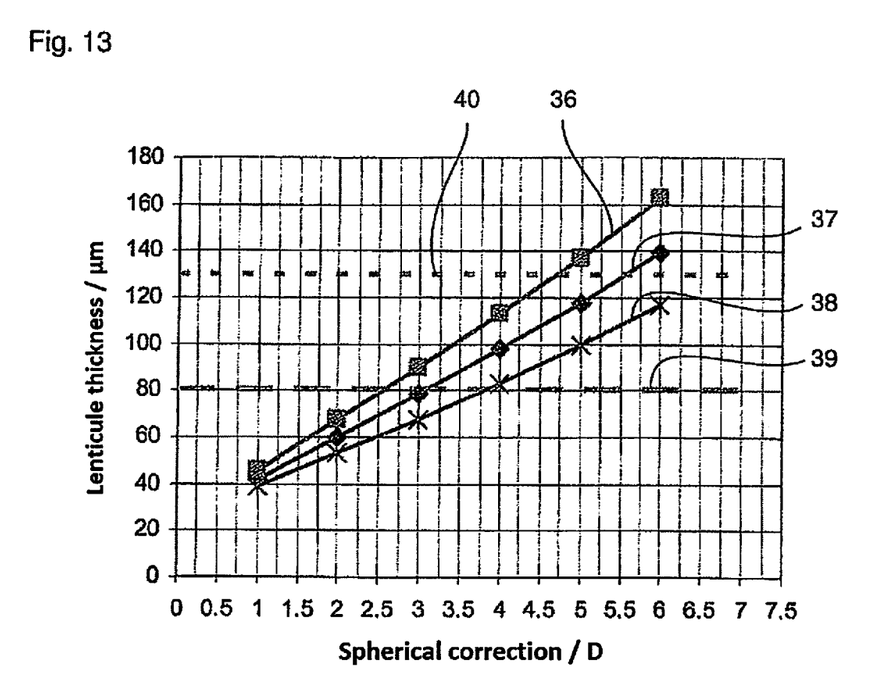
FIG. 13 is a representation to explain the possible spherical correction taking into account the minimum remaining cornea thickness.

In FIG. 13, the spherical correction which can be achieved is represented as a function of the lenticule thickness, wherein curve 36 shows the case in which the removed lenticule corresponds to the first lenticule-shaped intended volume (which, however, is not the case according to the invention). Curve 37 shows the case according to the invention, wherein the ratio of the refractive powers in the case of photopic and in the case of scotopic radius is 4/3. Curve 38 relates to the case in which the ratio of the refractive power in the case of the photopic radius to that in the case of the scotopic radius is 2 to 1. For the sake of simplicity, a cornea thickness of 500 µm and a distance between flap surface and cornea front surface of 120 µm are assumed. If a minimum residual thickness of the cornea 5 of 250 µm is required now, the maximum lenticule thickness must not exceed 80 µm, as indicated by dashed line 39. The maximum spherical correction can therefore be increased from the previously possible correction value of approx. 2.5 diopters to approx. 3.1 diopters for the curve 37 and approx. 3.75 diopters for the curve 38. With a minimum residual thickness of the cornea 5 of 300 µm, the maximum lenticule thickness can be 130 µm, as indicated by the dotted line 40. In this case an improvement from 4.75 diopters (curve 36) to, e.g., 5.5 diopters (curve 37) is possible.

A reduction in the maximum lenticule thickness can also be achieved in a myopia correction. Here too, the lenticule thickness for the correction of the myopia measured is first determined (steps S1 and S2), and is represented as a function of the radius in FIG. 14 as curve 42. By a suitable reduction in thickness such that the correction of refractive power becomes smaller from the center towards the edge, a lenticule profile according to curve 41 is achieved, whereby the maximum lenticule thickness can be reduced by 12.8 µm. In FIG. 15, in turn, the actual change in refractive power achieved in diopters is represented as a function of the pupil diameter in mm, wherein points 34 and 35 denote the photopic pupil and the scotopic pupil. In the example described here, an optical zone, or treatment zone, with a diameter of 7 mm was assumed, as indicated by arrow P3.

Figure 14:
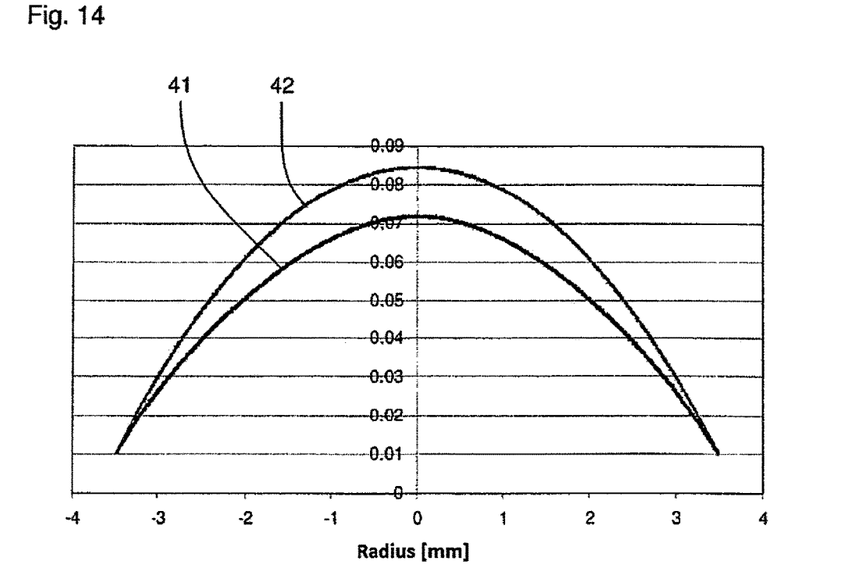
FIG. 14 is a diagram to explain the determination of the lenticule depth in a myopia correction.
Figure 15:
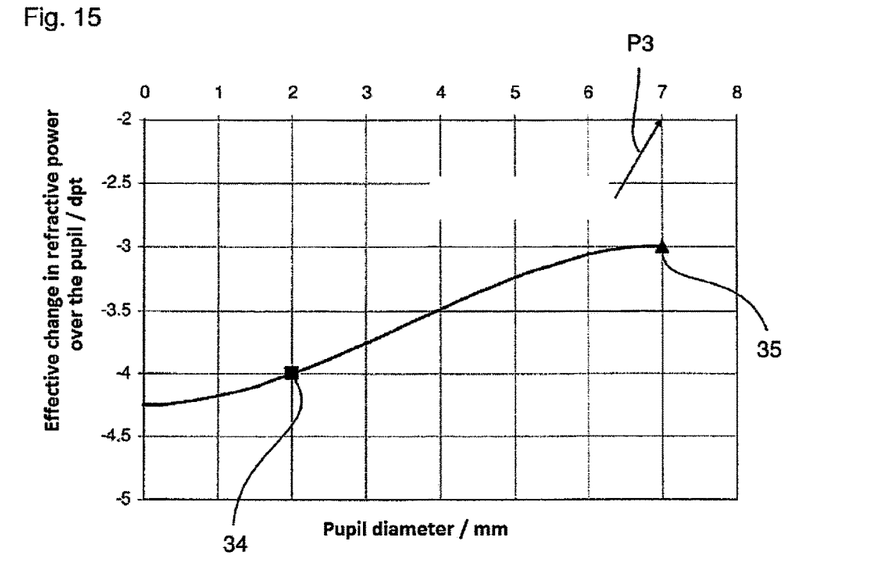
FIG. 15 is a diagram to explain the effective change in refractive power achieved in the myopia correction as a function of the pupil diameter.

Owing to the lenticule profile 41 chosen according to FIG. 14, the cornea front surface after the lenticule 18 has been removed is curved less in the center than at the edge, with the result that an oblate cornea 5 is present.

In the previously described embodiments, it has been assumed that the desired correction of defective vision is to be constant in the treatment zone. However, this need not be the case. Thus, the desired correction of defective vision can, for its part, already have a changing refractive index, as is described in detail, e.g., in connection with FIG. 9 of WO 2010/084162 A2. Starting from such a desired correction of defective vision, the second lenticule-shaped intended volume is then determined according to the invention such that the removal of such a separated lenticule from the cornea leads to an actual correction of defective vision which differs from the desired correction of defective vision more at the edge of the optical zone than in the center of the optical zone. Also in this case, the maximum thickness of the removed lenticule is reduced.

For ways of computationally determining the first lenticule-shaped intended volume, reference is made to the already-cited WO 2010/084162 A2. The methods of calculation described there can also be used here. Reference is also made to WO 2010/084163 A1 in relation to ways of precisely positioning the cornea as well as the curvature of the cornea by means of a contact glass (in particular the description on page 27).

The use of pulsed laser radiation is not the only way in which surgical refraction correction can be carried out. Rather, the determination described here of control data for operating the device can be used for almost any surgical procedure in which a volume is removed from the cornea by means of a device controlled by control data.

The invention claimed is:

1. A method for producing, providing and using control data for a laser apparatus of a treatment device for surgical correction of defective vision in an eye, the laser apparatus configured to cut a lenticule-shaped volume of corneal tissue of the eye by irradiation with laser radiation based on the produced control data, the method comprising:

computationally determining a desired correction of defective vision, using a controller of the treatment device that uses the laser apparatus for surgical correction of defective vision, based on measurement data of the eye, the desired correction corresponding to a lenticule-shaped comparison volume, the lenticule-shaped comparison volume being a volume that if removed from the cornea would cause the desired correction of defective vision, computationally determining, using the controller of the treatment device that uses the laser apparatus for surgical correction of defective vision, a lenticule-shaped intended volume of corneal tissue for removal from the eye based at least in part on the determined desired correction, the lenticule-shaped intended volume differing in shape as compared to the lenticule-shaped comparison volume, the lenticule-shaped intended volume being a volume that if removed from the cornea would cause an actual correction of defective vision in an optical zone in the eye, the optical zone defining a center at an optical axis of the eye and defining an edge, the edge being radially displaced from the center, and the actual correction differing from the desired correction of defective vision more at the edge of the optical zone than at the center of the optical zone, and producing the control data based on the lenticule-shaped intended volume, and transmitting the control data to the laser apparatus of the treatment device for controlling laser radiation of the laser apparatus so as to cut the cornea of the eye and isolate the lenticule-shaped intended volume of corneal tissue in the cornea of the eye, controlling laser radiation of the laser apparatus using the transmitted control data so as to cut the cornea of the eye and isolate the lenticule-shaped intended volume of corneal tissue in the cornea of the eye, wherein a thickness of the computationally-determined lenticule-shaped intended volume at the edge of the optical zone is less than a thickness of the lenticule-shaped comparison volume at the edge of the optical zone, such that removal of the lenticule-shaped intended volume from the cornea by the laser apparatus results in a lower maximum cutting depth in the cornea at the edge of the optical zone as compared to a maximum cutting depth in the cornea at the edge of the optical zone required for removal of the lenticule-shaped comparison volume.

2. The method according to claim 1, wherein the lenticule-shaped comparison volume is first computationally determined, and then the thickness of the lenticule-shaped comparison volume is computationally reduced in order to computationally determine the lenticule-shaped intended volume.

3. The method according to claim 1, wherein the lenticule-shaped intended volume is determined such that an actual correction of defective vision brought about by removal of the lenticule-shaped intended volume corresponds, in the center of the optical zone, to the desired correction of defective vision.

4. The method according to claim 1, wherein the lenticule-shaped intended volume is determined such that an actual correction of defective vision brought about by removal of the lenticule-shaped intended volume differs from the desired correction of defective vision such that a difference in thickness increases steadily in a radial direction from the center of the optical zone towards the edge of the optical zone.

5. The method according to claim 1, wherein a spherical aberration is subtracted from the lenticule-shaped comparison volume to determine the lenticule-shaped intended volume.

6. The method according to claim 1, wherein the lenticule-shaped intended volume is determined such that, after it has been removed, a front of the cornea is prolate if the desired correction of defective vision is a hyperopia correction.

7. The method according to claim 1, wherein the lenticule-shaped intended volume is determined such that, after it has been removed, a front of the cornea is oblate if the desired correction of defective vision is a myopia correction.

* * * * *

UNITED STATES PATENT AND TRADEMARK OFFICE
CERTIFICATE OF CORRECTION

PATENT NO. : 10,271,990 B2
APPLICATION NO. : 14/351854
DATED : April 30, 2019
INVENTOR(S) : Georg Sluyterman van Langeweyde, Gregor Stobrawa and Christoph Russmann It is certified that error appears in the above-identified patent and that said Letters Patent is hereby corrected as shown below:

On the Title Page

Item (72), under "Inventors", Line 3, delete "Christoph Russmann, Jena (DE)" and insert -- Christoph Russmann, Goettingen (DE) --, therefor.

In the Specification

In Column 6, Line 33, delete "correction, and" and insert -- correction; and --, therefor.

In Column 8, Line 27, delete "For example a" and insert -- For example, a --, therefor.

Signed and Sealed this
Seventh Day of January, 2020

Andrei Iancu
*Director of the United States Patent and Trademark Office*